United States Patent [19]

Watson, Jr.

[11] Patent Number: 4,831,325
[45] Date of Patent: May 16, 1989

[54] CAPACITANCE MEASURING CIRCUIT

[75] Inventor: Charles W. Watson, Jr., North Wales, Pa.

[73] Assignee: General Signal Corporation, Stamford, Conn.

[21] Appl. No.: 32,664

[22] Filed: Apr. 1, 1987

[51] Int. Cl.[4] .................. G01R 27/26; G01L 9/12
[52] U.S. Cl. ................... 324/61 R; 324/60 CD; 324/60 C; 73/724
[58] Field of Search ........... 324/60 CD, 61 R, 60 C; 307/246, 110; 73/336.2, 304 C, 718, 724; 364/551

[56] References Cited

U.S. PATENT DOCUMENTS

| | | | |
|---|---|---|---|
| 3,221,247 | 11/1965 | Samuelian | 324/61 |
| 3,903,478 | 9/1975 | Stuart et al. | 324/61 R |
| 4,054,833 | 10/1977 | Briefer | 324/60 C |
| 4,096,758 | 6/1978 | Moore | 73/718 |
| 4,250,452 | 2/1981 | Gray et al. | 328/1 |
| 4,392,378 | 7/1983 | Pitches et al. | 73/304 C |
| 4,423,371 | 12/1983 | Senturia et al. | 324/61 R |
| 4,547,725 | 10/1985 | Oetiker et al. | 324/61 R |
| 4,558,595 | 12/1985 | Kompelien | 324/61 R X |
| 4,568,875 | 2/1986 | Piso et al. | 324/61 R |
| 4,656,871 | 4/1987 | Czarnocki | 73/724 |

FOREIGN PATENT DOCUMENTS 61-235745 10/1986 Japan .
2020434A 11/1979 United Kingdom .

OTHER PUBLICATIONS

Iwai et al.; Capacitance Measurement Circuits in VSLI Structures, IEEE Trans. on Electron Devices, vol. ED-29, No. 10, Oct. 1982, pp. 1622-1626.
Matsumoto et al., A Switched-Capacitor Digital Capacitance Meter; IEEE Trans on Inst., vol. IM-35, No. 4, Part 2, Dec. 1986, pp. 555-559.
"Design of Nonlinear Analog Switched-Capacitor Circuit Building Blocks" by Hosticka et al., IEEE Transactions and Systems; Apr. 1984, pp. 354-367.
An MOS Switched-Capacitor Readout Amplifier for Capacitive Pressure Sensors by Y. E. Park and K. D. Wise, IEEE Proceedings of 1983, Custom Integrated Circuits Conference.
Precision Measurement Technique of Integrated MOS Capacitor Mismatching Using a Simple On-Chip Circuit by Masakazu Furukawa, Hidetoshi Hatano, and Koji Hanihara, IEEE Trans. on Elect. Dev., vol. ED-33, No. 7, Jul. 1986.
All-MOS Charge Redistribution Analog-to-Digital Conversion Techniques—Part 1 and Part 2, by James L. Creary and Paul R. Gray, IEEE Journal of Solid State Circuits, vol. SC-10, No. 6, Dec. 1975.

Primary Examiner—Reinhard J. Eisenzopf
Assistant Examiner—Jack B. Harvey
Attorney, Agent, or Firm—Harold Huberfeld; William G. Miller, Jr.

[57] ABSTRACT

A variable capacitor, which may be a humidity sensitive capacitor, and a fixed reference capacitor are connected at a node. The node is clamped at a reference potential during a first phase of a two phase measuring cycle as the variable capacitor is charged to a fixed voltage and the fixed capacitor is charged to a feedback voltage. The node is unclamped during the second phase and the capacitors are connected in a series loop to allow a redistribution of the charge in the capacitors or force a reversal of that charge with a voltage source. The deviation of the node from its reference potential after charge redistribution occurs is used as input to a feedback circuit which integrates that deviation over a number of cycles until it provides a feedback voltage of magnitude sufficient to cause the node deviation to be reduced to zero. A second reference capacitor can be supplied to provide an offset. The capacitors are constructed by simultaneous deposition on a substrate of a first plate followed by a dielectric film and a second plate. The second plate of the variable capacitor is porous to admit water molecules and the second plate of the fixed capacitor is impervious to water. The simultaneous deposition provides similar characteristics for the capacitors.

26 Claims, 4 Drawing Sheets

INVERTER TRANSFER
CHARACTERISTIC

CAPACITANCE MEASURING CIRCUIT

BACKGROUND OF THE INVENTION

This invention relates to a method and apparatus for measuring the capacitance of variable capacitors and to methods and apparatus for measuring relative humidity using capacitive sensors whose capacitance varies with relative humidity. This invention also relates to methods and apparatus for measuring other variables by using capacitive sensors whose capacitance is related to the magnitude of the variable to be measured.

Capacitive humidity sensors may, for example, be constructed by laying a first conductive plate area on a silicon chip, then covering that area with a polymer, such as a polyimide, of desired thickness as a dielectric, and then depositing the second plate as a conductive layer over the dielectric. The polyimide forms a thin, water absorbing dielectric film whose dielectric constant varies in proportion to the concentration of the absorbed water so that the capacitance of the combination varies with the humidity of the surrounding region.

Another example of a capacitive sensor is the capacitive pressure transducer. One form these transducers take at the present involves the use of a silicon diaphragm which is bonded between two silicon plates to form a capacitor on each side of the diaphragm. Those capacitors are responsive to the difference in pressure between the two sides of the diaphragm. The dielectric between the plates in these structures is usually silicone oil.

In both the capacitive pressure transducer and the capacitive humidity sensor, it has been found to be desireable to integrate the measuring circuit and the capacitive sensor onto a single monolithic silicon chip, if that is possible. By so doing, the sensor and the other capacitive elements of the circuit can easily be constructed on the substrate at the same time so that they have the same plate dimensions and the same dielectric thickness. This gives all of the capacitors the same characteristics making it possible to incorporate them into measuring circuits without the need for either electrically trimming those circuits or physically trimming the plate dimensions to attempt to match their characteristics. Also, by using a single chip the components of the circuit will be subjected to the same ambient conditions so that temperature and pressure variations will affect the components of the circuit by the same amount. If placing all of the measuring circuit components on a single chip is not possible, then it has been found to be desirable to make the measuring circuit elements as nearly similar as possible and place them as close as possible to the sensor so that they have very similar characteristics to those of the sensor and are subjected to ambient conditions closely approximating those to which the sensor is subjected.

Typically, the prior art relating to the measurement of capacitance requires the use of resistors. It is well known that large accurate resistors require a significant area on a chip. Also, it is desirable to avoid the need to depend on the accuracy of the parameters introduced into a circuit by a resistor. Similarly, it is desirable to avoid variation which can be introduced by a semiconductor device or by a multivibrator. For these reasons improvements can be foreseen if it is only necessary to depend on the parameter values of capacitors and external reference voltages. One such improvement would be minimizing the cost of manufacture. This benefit is evident when one considers the fact that capacitors can be matched during the mask and layout stage of the semiconductor manufacturing procedure, and the fact that the possibility of closely matching those elements makes trimming unecessary even when one must provide finished units which will all have the same span and the same offset so that they can be used interchangeably without the need for calibration.

Switched capacitor circuits are known in the field of A/D converters. Such circuits have used switched capacitors which are effective to change the input of an amplifier circuit in the manner shown in the publication "Intuitive IC CMOS Evolution" by Frederiksen, at pages 103–105. In those circuits, there is shown a sampled data comparator which consists of CMOS analog switches, a string of capacitively-coupled logic inverters for voltage gain, and capacitors, some of which convert from voltage to charge and others of which serve to couple the converters. The particular circuits described, while not useful in measuring capacitance, do show the use of a string of capacitively coupled logic inverters providing amplification for a switched-capacitor circuit, where the capacitors in the circuit are zeroed by shorting out the logic inverters. That approach is used to provide the amplification and the setting-up of the capacitors in one form of the switched capacitor circuit of the present invention.

It is an object of this invention to provide an improved capacitance measuring circuit and, more particularly, one which will measure the capacitance of a capacitive sensor by using only capacitors and other circuit components which can be easily integrated onto a small monolithic silicon chip so as to avoid the need for either physically trimming the components or electrically trimming the associated measuring circuit for calibration purposes.

It is a further object of this invention to provide a measuring circuit for measuring the capacitance of a capacitive humidity sensor so that a minimum of trimming is needed even though it is not possible to integrate all of the capacitors of the measuring circuit onto the same silicon chip.

In addition, it is an object of this invention to provide a measuring circuit for measuring the capacitance of a capacitive humidity sensor in a manner which will make the measurement immune to drift with changes in temperature or humidity.

SUMMARY OF THE INVENTION

In carrying out the present invention there is provided a method and a circuit for measuring the capacitance of a variable capacitor such as a capacitive sensor whose capacitance varies with the magnitude of a variable to be measured. The circuit requires at least one reference capacitor, which is charged to a variable output voltage during the first phase of a two phase measuring cycle while the variable capacitor is charged to a fixed voltage. The capacitors are connected in a loop during the second phase of the measuring cycle. The potential at the junction between the capacitors is then compared with a predetermined balance value and the output voltage is iteratively varied in a direction to reduce the deviation from the balance value to zero so that the output voltage will be proportional to the capacitance of the variable capacitor.

When it is desired to convert the output voltage to a digital readout by using an A/D converter which has differential inputs for both the unknown and the reference potential and a digital indicator, the present invention can include a circuit for tailoring the inputs to the A/D converter so that the full scale range and zero offset of the output voltage, for the range of humidity being measured, generates a full scale indication on the indicator. This circuit includes a potentiometer supplied from the sampling voltage and connected with its tap supplying a potential which will change the magnitude of the unknown input depending on the position of said tap so that the input of the converter is adapted to the zero offset. Also included is a network which is supplied from the tap and from a voltage divider across said sampling voltage so that the output of the network is effective to modify the reference inputs to adapt the converter to the change in the output voltage which represents full scale range. The potentiometer tap must be adjustable to provide the necessary trimming when the reference capacitor does not exactly match the unknown variable capacitor, as would be the case if they were manufactured by integrated circuit techniques on the same substrate and at the same time. If they are manufactured to be exactly alike, the tap can be a fixed point since trimming is not needed.

Where the variable capacitor is a humidity sensor, one form of the invention contemplates manufacturing both capacitors at the same time with the same materials by integrated circuit techniques on the same substrate in order to perfectly match the two capacitors. Sealing the reference capacitor from exposure to the atmosphere whose humidity is to be measured is then necessary to prevent it from changing capacitance with humidity changes.

DESCRIPTION OF THE PREFERRED EMBODIMENTS

Figure 1:
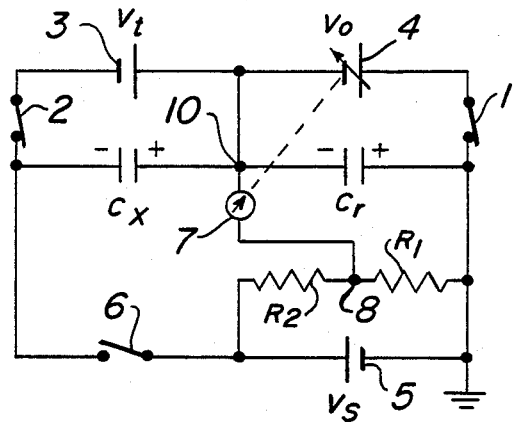
FIG. 1 shows a simplified circuit diagram of one form of the invention.

FIG. 1 shows a simplified circuit which illustrates the operation of both the method and apparatus of this invention. In FIG. 1 a variable capacitor, $C_x$, such as a capacitive sensor for measuring relative humidity, is connected in series with a fixed or reference capacitor, $C_r$, at a node 10. In a first phase of a measuring cycle having two non-overlapping phases, the switches 1 and 2 are closed, as shown, so that the fixed voltage source 3 provides a voltage $V_t$ across $C_x$ and the variable voltage source 4 provides a voltage $V_o$ across the capacitor $C_r$. In the second phase of the measuring cycle the capacitors $C_x$ and $C_r$ are connected in series with a fixed sampling voltage, as supplied by source 5, by the making of the switch 6 and the disconnection of the switches 1 and 2. The charges in the capacitors are allowed to redistribute themselves, and then the high impedance detector 7 detects or measures the difference between the existing potential at the junction between the capacitors and a predetermined balance value for that potential. In FIG. 1 that difference is detected or measured by looking at the difference between the potential at the node 10 and at a reference point 8, the balance value. If the deviation or difference is not zero then the variable voltage source 4 is modified. In the circuit shown, the modification would be in a direction corresponding with the deviation detected. In other words, if the potential difference between node 10 and reference point 8 is negative the voltage $V_o$ is decreased. The reference point 8 may be at any of a number of potentials; for example, circuit common potential, which allows elimination of the resistors $R_1$ and $R_2$, or a potential representing half of the drop across the source 5, in which case the resistors will be of equal value.

The value of the voltage $V_o$ will be found to be proportional to the changing value of the capacitance of capacitor $C_x$ if the deviation of the difference detected by 7 from the predetermined balance value is kept at zero. This results from the fact that, as the capacitance of $C_x$ changes with a resulting change in the charge it carries after its charging in the first phase, the charging voltage on $C_r$ is changed to similarly change the charge it carries. Then, the redistribution of charges which occurs during the second phase will provide a changed balance between the resulting voltages across the two capacitors such that there will be a reduction of the deviation detected by the detector. After a number of iterations in the proper sense the deviation will reach zero and $V_o$ will be a measure of the capacitance of $C_x$.

Proper operation of the circuit of FIG. 1 does not require that the sampling voltage be a certain polarity of magnitude-indeed the magnitude may be zero-or that the output voltage $V_o$ be a certain polarity. The reversal of the polarity of the sampling voltage wil only invert the relationship of $V_o$ and the variable capacitance being measured, whereas the polarity of $V_o$ will generally be a function of other parameters.

Figure 2:
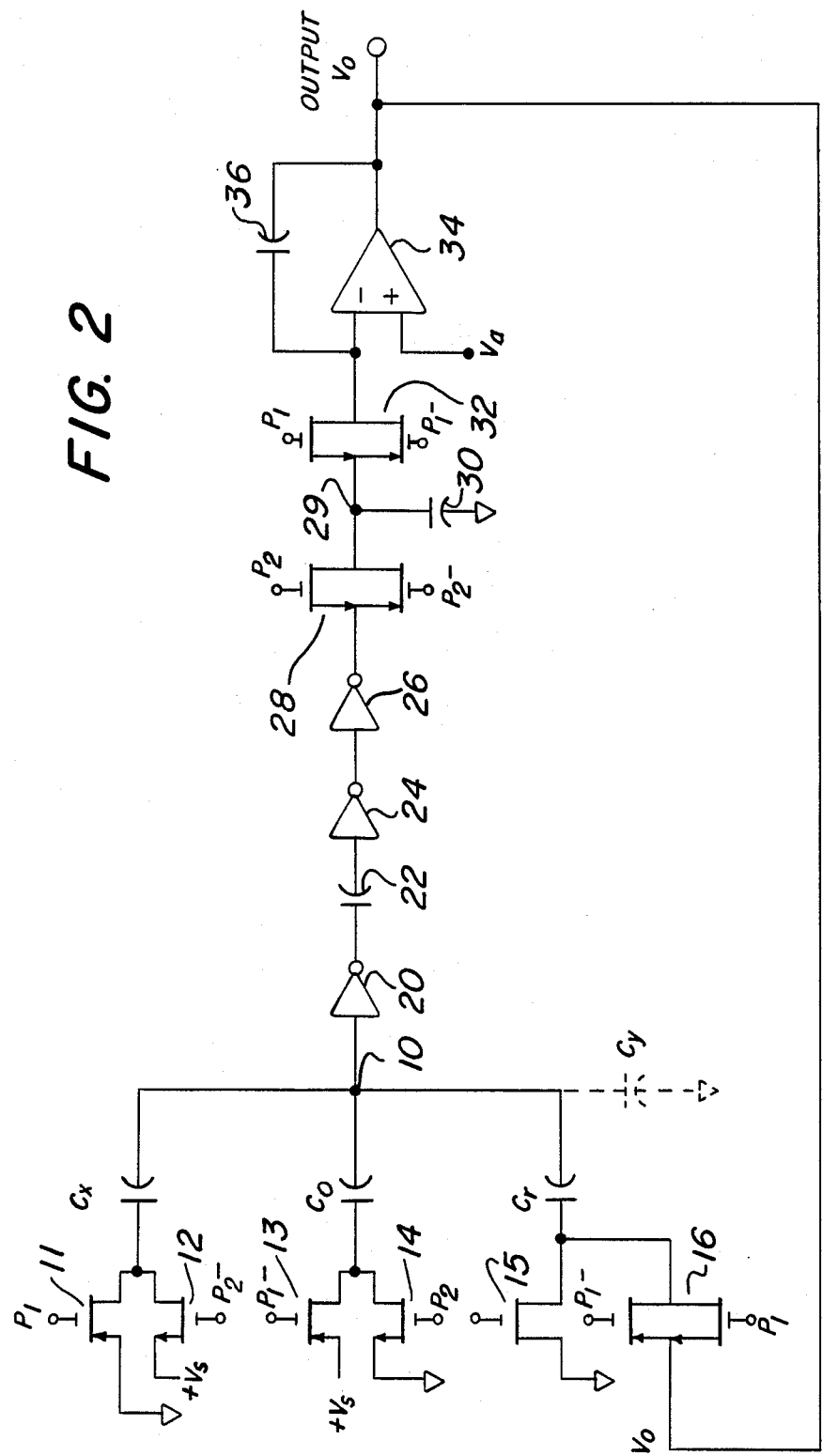
FIG. 2 shows a more detailed circuit diagram of another form of the invention.

In FIG. 2, there is shown in more detail a circuit which follows the principles of operation illustrated by FIG. 1. In FIG. 2, the reference point 8 of FIG. 1 is circuit common potential and the detector 7 is comprised of cascaded logic inverters and an integrating amplifier with its associated switches. The predetermined potential difference across the reference capacitor to be detected by the detector 7 as an indication of balance is the trigger voltage of the inverters as established by the shorting of their inputs and outputs. That trigger voltage is also the voltage to which $C_x$ is charged, namely $V_t$. in FIG. 2, the variable capacitor $C_x$, which may be a capacitive humidity sensor, is connected in a network with reference capacitor $C_r$ and an additional reference capacitor $C_o$ by connecting one terminal of each to the node 10. The other terminals of these capacitors are selectively connected by way of switching elements 11-16 to either the output voltage, $V_o$, or to a predetermined sampling voltage, $V_s$, or to circuit common. For the purpose of this circuit the switching elements 11-15 are MOS transistor switches and switch 16 is a CMOS switch. In addition to the 5 capacitors mentioned, there will, of course, be a stray capacitance, which is represented in FIG. 1 by $C_y$. As will be demonstrated later, the stray capacitance will only have a second order effect.

Figure 5:
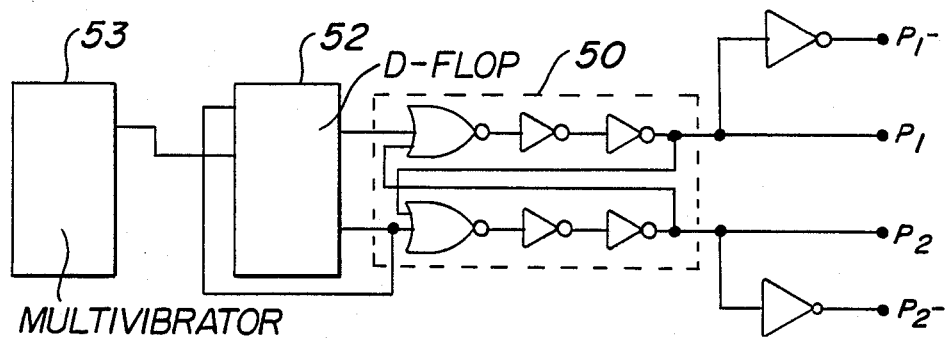
FIG. 5 shows a circuit diagram of a clock circuit which can be used to switch the elements of FIG. 2.

In the operation of this circuit the switches 11, 13, and 16 are closed, and the remainder of the switches are open during the first, setup phase, $\phi_1$, of a two phase clock which is used to time the two phases of the measuring cycle. This clock, which is shown in FIG. 5 and described subsequently, provides two non-overlapping clock signals of both polarities, $P_1$ and $P_1-$, during the first phase; and $P_2$ and $P_2-$ during the second, or sampling phase, $\phi_2$. During the second, sampling phase the switches 12, 14 and 15 are closed and switches 11, 13, and 16 are open.

As shown in FIG. 2, the node 10 is connected to the input circuit of a logic inverter, which is in turn connected through capacitor 22 to another logic inverter 24. The output of inverter 24 is then connected through still another logic inverter and through CMOS switch 28 to terminal 29, which connects through capacitor 30 to circuit common. The terminal 29 is, as shown, connected through CMOS switch 32 to the inverting input of an operational amplifier 34. That amplifier has the capacitor 36 in its negative feedback circuit so as to form an integrating amplifying circuit. Also, as shown, the non-invertinng input to amplifier 34 is connected to a voltage $V_a$, and the output of the amplifier is an output voltage $V_o$, which is fed back to one side of switch 16 and is also provided to any indicating or recording circuits which may be utilized to obtain a readout of the measured capacitance value of $C_x$.

The switches 28 and 32 are driven by the clock signals so that 32 is closed and 28 is open during the setup phase, when the charge on capacitor 30 is effective to cause the output of amplifier 34 to change and hence the charge on capacitor 36 to change until the potential at the inverting input of the amplifier is equal to the potential at the non-inverting input, $V_a$. This provides an output $V_o$ which is the integral of the voltages to which the capacitor 30 is charged during consecutive sampling phases. During the sampling phase, the switches 28 and 32 are reversed and the capacitor 30 is charged from the output of the logic inverters in proportion to the change in potential at node 10 which occurs upon switching from the setup phase to the sampling phase.

It will be evident that the timing of the clock and the parameters of the capacitors $C_x$, $C_o$ and $C_r$ must be such that the capacitors are allowed to obtain their full charge as appropriate for the voltages applied to them during each phase. Thus, the transients caused by the switching of the connections are allowed to settle out before the circuit is again switched.

Figure 3:
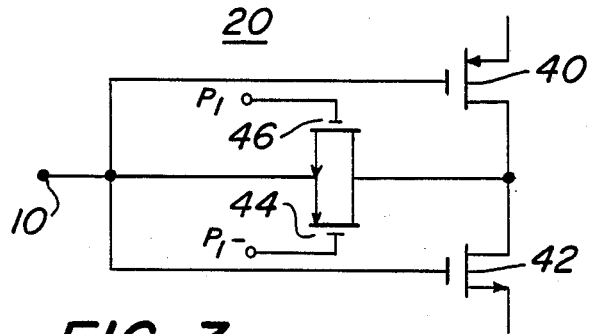
FIG. 3 shows a circuit diagram of a switching circuit of the type used to short out the logic inverters of the amplifier in FIG. 2.

FIG. 3 shows a circuit which can be used for the logic inverter 20. In that circuit the CMOS amplifiers 40 and 42 provide the amplification and the logic inversion while the CMOS switches 44 and 46 provide the shorting of the amplifier's input and output as is required during the setup phase of the measuring cycle in order to keep the node 10 at a fixed potential. In this case that fixed potential will be the threshold potential of the logic inverters, known as the trigger voltage, $V_t$, which during the first phase is $V_{t1}$. The switches 44 and 46 are closed to short the input and output of the inverter during the setup phase and are open during the sampling phase of the measuring cycle so that the node 10 is clamped at the threshold potential, $V_{t1}$, during the setup phase and potential at the node 10, $V_{t2}$, is allowed to float during the sampling phase.

It is, of course, evident that the logic inverter 20 will not draw any significant current during the sampling phase, but will supply any necessary current to charge the capacitors during the setup phase to hold node 10 at $V_{t1}$. The other logic inverters 22 and 24 can be constructed as shown for inverter 20 in FIG. 3. The inverters 22-24 will also have their inputs tied to their outputs during the setup phase; and capacitors, such as capacitor 22, can be provided between inverters for accomodating any differences between their individual threshold voltages. In FIG. 2 only the interstage capacitor 22 is shown, for it is not always necessary to incorporate such capacitance between the remaining stages. As is characteristic of logic inverters of the type described, the output of these units will go low when the input deviates from the threshold voltage in a positive direction and will go high when the deviation is in the opposite direction. This characteristic is illustrated in inverter transfer characteristic shown in FIG. 4 which shows $V_o$ vs. $V_{in}$. It will be noted that any small change of the input from the trigger voltage, $V_t$, will cause a considerable change in the output. The slope of the steep portion of the characteristic will be dependent on the particular way in which the element is manufactured.

FIG. 5 shows a clock circuit which can be used to time the two phases of the measuring cycle. In this circuit a non-overlapping clock module 50 is driven by D-flop 52 whose input is from the multivibrator 53. As shown, the output of the clock module is the plus and minus potentials of $\phi_1$, $P_1$ and $P_1-$, and the plus and minus potentials of $\phi_2$, $P_2$ and $P_2-$.

The operation of the measuring circuit of FIG. 2 may be considered by examining the charges on the capacitors $C_x$, $C_o$ and $C_r$ during the two phases $\phi_1$ and $\phi_2$.

During $\phi_1$ the voltage on node 10 is held at the trigger voltage, $V_{t1}$, and during $\phi_2$ the voltage on node 10 is allowed to float at voltage $V_{t2}$, as determined by the charges on the capacitors in the network. The charges on the capacitors are as follows:

| for $\phi_1$ | for $\phi_2$ |
|---|---|
| $Q_{x1} = C_x(-V_{t1})$ | $Q_{x2} = C_x(V_s - V_{t2})$ |
| $Q_{o1} = C_o(V_s - V_{t1})$ | $Q_{o2} = C_o(-V_{t2})$ |
| $Q_{r1} = C_r(V_o - V_{t1})$ | $Q_{r2} = C_r(-V_{t2})$ |
| $Q_{y1} = C_y(-V_{t1})$ | $Q_{y2} = C_y(-V_{t2})$. |
| If $\Delta Q = Q_1 - Q_2$ and $\Delta V_t = V_{t2} - V_{t1}$, | |
| then $\Delta Q_x = C_x(-V_s + \Delta V_t)$, | |
| $\Delta Q_o = C_o(V_s + \Delta V_t)$, | |
| $\Delta Q_r = C_r(V_o + \Delta V_t)$, | |
| and $\Delta Q_y = C_y(\Delta V_t)$. | |

Since the total change in the node 10 must be zero, then $$\Delta Q_x + \Delta Q_o + \Delta Q_r + \Delta Q_y = 0;$$

and if
$$\Sigma C = C_x + C_o + C_r + C_y,$$

then
$$C_x(-V_s + \Delta V_t) + C_o(V_s + \Delta V_t) + C_r(V_o + \Delta V_t) + C_y(\Delta V_t) = 0,$$

and
$$V_s(C_o - C_x) + C_r V_o + \Sigma C \Delta V_t = 0.$$

Since $\Delta V_t = 0$ is the network condition defined as balance, and $V_o$ is a measure of $C_x$;

$$V_o = \frac{V_s(C_x - C_o)}{C_r},$$

Thus, it can be seen that the output voltage is a function of the variable capacitance $C_x$ plus a constant offset determined by the capacitance of $C_o$.

It will be evident to those skilled in the art that the capacitor $C_o$ and its associated switching elements can be omitted if it is not desired to offset the relationship between the output voltage and the indicated value of $C_x$.

It is also evident that the value of the stray capacitance $C_y$ does not affect the accuracy of the resulting measure of the variable capacitor since it does not appear as a term in the final relationship between $C_x$ and $V_o$, as derived above. The stray capacitance, $C_y$, does, however, affect the sensitivity.

The MOSFET switches 44 and 46 will have capacitance between the gate, on one side, and the source and drain, respectively, on the other side. These capacitances will cause error, but that error can be minimized by using small transistors for this switching service and by using similar sizes so as to closely match them.

The voltage $V_a$ on the non-inverting input of the amplifier 34 should be approximately equal to $V_s/2$. If $V_a$ is not exactly equal to $V_s/2$ the effect is only to introduce a small asymmetry in step size for raise steps as compared with lower steps in the integrator output $V_o$.

As has been stated, where the variable capacitor is a capacitive humidity sensor, it is desirable to have all capacitors in the measuring network on the same substrate and to construct them with the same plate area and the same dielectic constant. The area of the plates can be carefully controlled by photolithography, but the thickness of the dielectric and hence the dielectric constant is not as easily controlled. It can, however, be matched to better than 0.1% by known techniques which use the same substance for all capacitors in the network. Care must be exercised in completely sealing the capacitors $C_o$ and $C_r$ from humidity, but $C_x$ must allow moisture to quickly penetrate the dielectric in order to obtain fast response to humidity changes.

Figure 6:
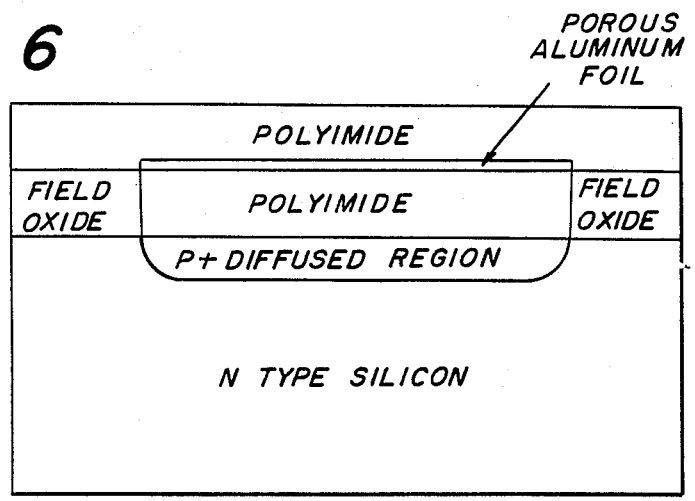
FIG. 6 shows a cross section of one form of a capacitive humidity sensor constructed using integrated circuit techniques.

The capacitor $C_x$ may be constructed as shown in FIG. 6 using well known integrated circuit techniques. In this structure the n-type silicon has a p+diffused region forming one plate of the capacitor. That plate is covered by the polyimide dielectric which is bounded by a field oxide. Over the dielectric is deposited an aluminum foil as the second plate of the capacitor. This foil is sufficiently thin so that it allows the water molecules to permeate the dielectric from the surrounding atmosphere after it has permeated the protective coating of polyimide covering the foil.

Figure 7:
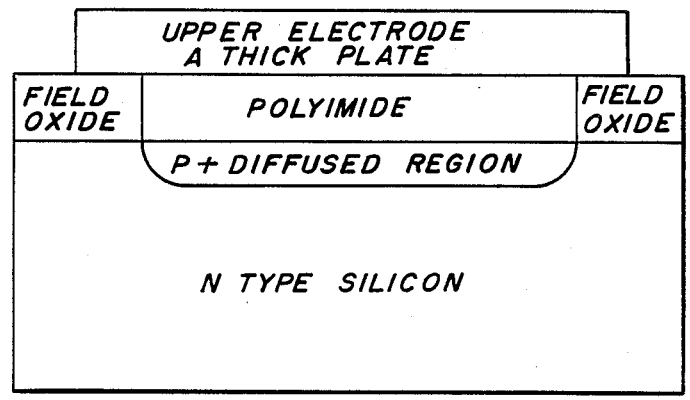
FIG. 7 shows a cross section of one form of a reference capacitor useful in the circuits of FIGS. 1 and 2.

The capacitors $C_o$ and $C_r$ can be constructed as shown in FIG. 7, in which the second electrode is constructed of a thick aluminum plate instead of a thin foil as in FIG. 6. The thick plate is designed to prevent the water molecules from permeating to the dielectric of these capacitors, for they must not be sensitive to changes in the relative humidity of the surrounding atmosphere. The polyimide protective coating shown in FIG. 6 can be omitted since it is not necessary to protect the top plate from contaminents.

Figure 8:
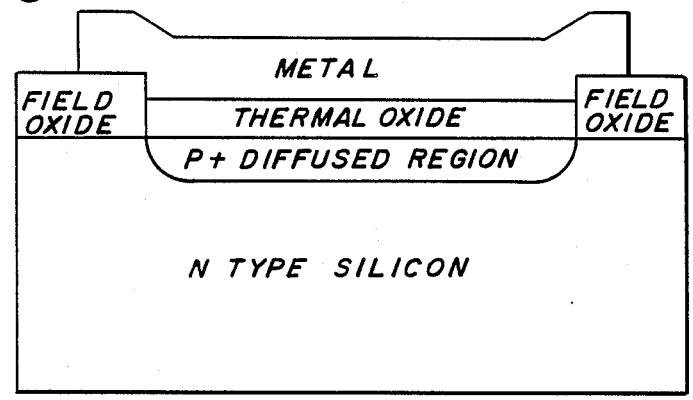
FIG. 8 shows a cross section of one form of the reference capacitor useful in the circuits of FIGS. 1 and 2 when it is desired not to have the reference capacitor sensitive to changes in humidity.

In applications where it is not possible to protect the capacitors $C_o$ and $C_r$ from the changes in humidity of the surrounding atmosphere, it is desirable to construct these capacitors differently so that they will not have a dielectric which changes its dielectric constant with changes in the humidity of the surroundings. For this type of service the capacitors $C_o$ and $C_r$ can be constructed as shown in FIG. 8 In that arrangement, it has been found useful to use $SiO_2$ as the dielectric. That material is not humidity sensitive so there is no need to seal the capacitors from water vapor. Using a different dielectric as compared to that use for $C_x$ will, of course, cause the capacitors $C_o$ and $C_r$ to fail to track $C_x$ with changes in temperature and humidity. More importantly, it will cause the circuits to have different span and range magnitudes due to the fact that the capacitor $C_x$ is not being produced at the same time and by the same process as $C_o$ and $C_r$ and therefore can not be expected to have exactly the same characteristics.

By way of example, $C_x$ can have a value of 8-10 pf, $C_o$ can have a value of 7 pf, and $C_r$ can have a value of 3 pf. The voltage $V_a$ can be 2.5 volts and $V_t$ will normally be approximately 2.5 volts. $V_s$ can be in the area of 5-6 volts. Clock frequencies on the order of 8 Khz have been used so that the capacitors will be allowed to charge completely during each phase of the measuring cycle. Capacitor 22 can be 20 pf and capacitor 30 can be 0.3 pf with capacitor 36 having a value of 200 pf. The voltage $V_o$ will vary in a range between 1-5 volts which provides a desirable voltage range for use in measuring systems.

In another form the present invention could use a digital counter coupled to a digital to analog converter in place of the integrating amplifier of FIG. 2.

Still another form of the present invention can utilize an analog to digital converter at the output of the integrating amplifier of FIG. 2 when it is desirable to obtain a digital readout.

Figure 9:
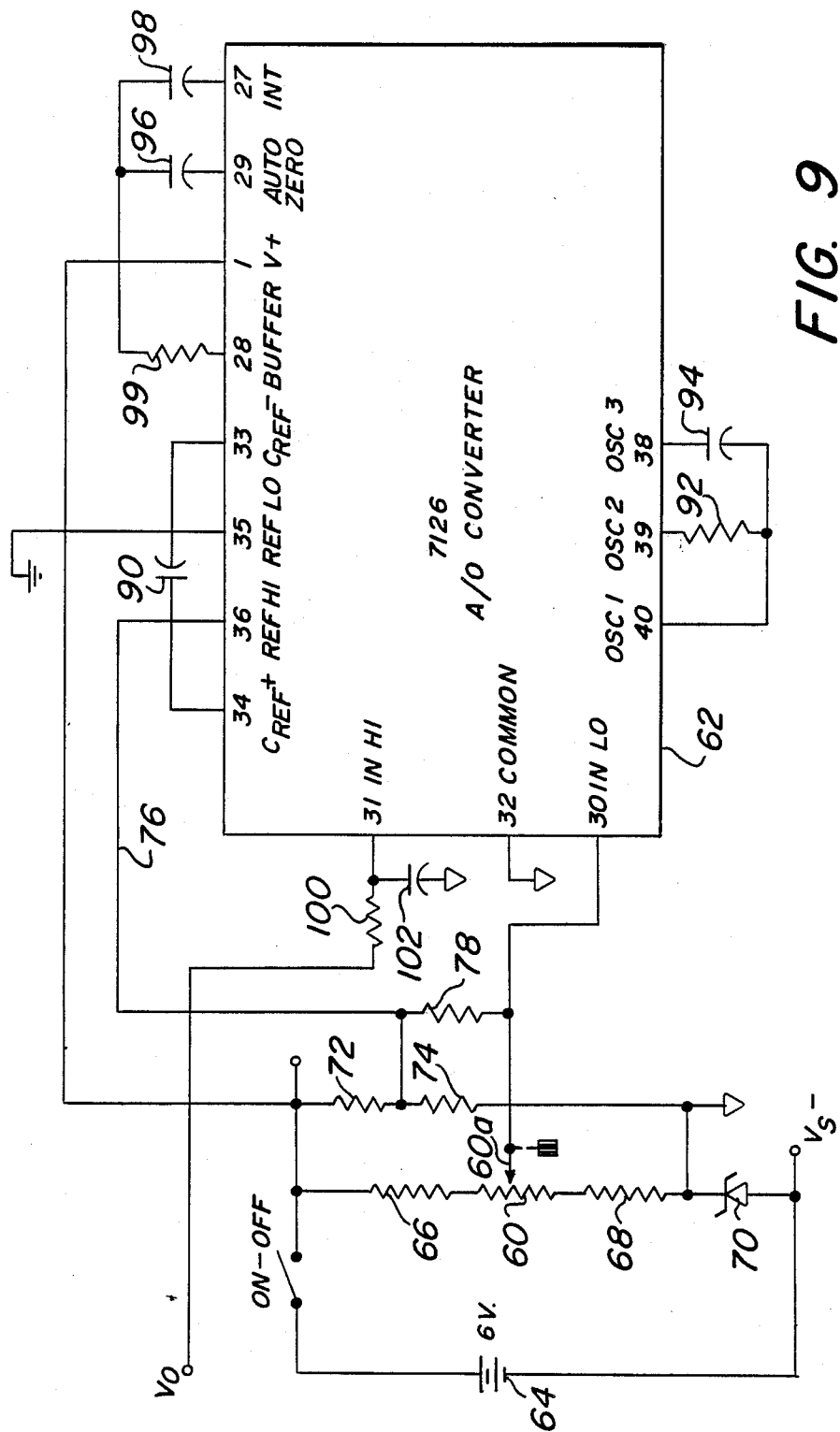
FIG. 9 is a circuit diagram of a circuit which can be used to connect the circuit of FIG. 1 to a 7126 A/D converter.

FIG. 9 illustrates a useful circuit for coupling the integrating amplifier of FIG. 2 to an analog to digital converter, such as a CMOS TSC7126 as manufactured by Teledyne Semiconductor and shown in their Data Acquisition Design Handbook of 1984, on page 7-73.

This unit provides a digital readout of 2000 counts. In order to provide for a scale factor other than unity, circuitry is required to determine the reference voltage for the A/D converter to accomodate the scale factor. Also, it is necessary to accomodate the offset at the zero humidity point by introducing an appropriate voltage at the low input terminal, IN LO, of the 7126. The circuit of FIG. 9 is arranged to provide these accomodations and to provide them in such a way that there is no necessity for making more than one potentiometer adjustment when one is using capacitors $C_o$ and $C_r$ of the type shown in FIG. 8. This simplifies the manufacture of the circuit of FIG. 9 considerably, for it is only necessary to adjust the circuit at one value of relative humidity instead of two in calibrating the units so that they will be interchangeable. Separate adjustments at different humidities would normally be required for offset and range.

The factors which must be kept in mind to understand the following explanation of the circuit of FIG. 9 are:

1. The dielectric of the measuring capacitor $C_x$ is of different material (a polyimide) than the dielectric of $C_o$ and $C_r$ ($SiO_2$). Thus, the capacitance of the measuring capacitor varies with humidity while the capacitance of the others do not.

2. $C_o/C_r$ is a constant for each circuit since the two capacitors are manufactured at the same time by the same process so that their characteristics are inherently the same.

3. $C_x/C_r$ varies from unit to unit due to variations in the manufacturing processes by which the two capacitors are made.

4. The capacitance of $C_x$ at full scale (100% relative humidity) is designated as $C_x(100)$ and the capacitance of $C_x$ at 0% relative humidity is designated as $C_x(0)$. The ratio $C_x(100)/C_x(0)$ is designated as $\alpha$.

5. $\alpha$ is a constant.

6. A/D converters, such as the 7126, have differential inputs for both the measured variable and the reference voltage.

It is evident from the above that it is desired to provide a circuit that can correct for $C_x/C_r$ and, as stated, it is desired to do this with a single potentiometer.

In FIG. 9 the offset of the range to be measured is accomodated by adjusting potentiometer tap 60a of potentiometer 60 to provide the required input to the IN LO terminal of the A/D converter 62, namely at pin 30. The potentiometer is supplied by a source of emf, 64, shown a 6 volt source, which supplies the series circuit shown as including resistors 66 and 68 in series with the potentiometer 60 and a zener diode 70. The zener diode is incorporated into the circuit to provide a negative power source for other components of the circuit.

The following equation may be written to express the quantity $C_x(100)-C_x(0)$, which shall be referred to as the gain G.

$$G=(\alpha-1)C_x(0)(V_s)/C_r$$

Since $V_{os}$, the output voltage of the circuit of FIG. 2 at 0% humidity, is as follows $$V_{os}=C_x(0)-C_o(V_s)/C_r$$

then
$$C_x(0)=(V_{os}C_r)/V_s+C_o,$$

and substituting;
$$G=(\alpha-1)V_{os}+((\alpha-1)C_o)/C_rV_s.$$

Figure 4:
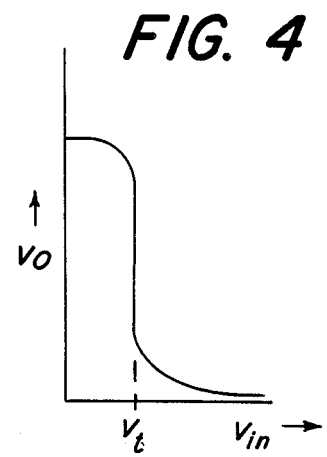
FIG. 4 shows a graphical representation of the transfer characteristic of the logic inverters of FIG. 2.

Since $\alpha$ and $C_o/C_r$ are constants, the latter term in the above equation can be represented by a divider on $V_s$. This is shown in FIG. 4 as the divider which consists of the resistors 72 and 74. Thus, the voltage introduced to the REF HI pin 36 over line 76 accomodates for the constant term of the equation. The first term is taken care of by resistor 78 which forms part of another divider circuit with resistor 72 and thus also influences REF HI. REF LO, pin 35, is connected to circuit common, as shown. The result of the divider and resistor 78 which together provide the input to pin 36 is to accomodate the span of the measuring circuit to the span of the A/D converter so that the voltage $V_o$ which corresponds to 100% relative humidity, for example, will cause the readout of the 7126 to be full scale.

The reference capacitor for the 7126 is shown as capacitor 90 and may have a value of 0.1 f. The external oscillator circuit provided for the 7126 is shown connected to pins 38, 39 and 40. This circuit includes the resistor 92 of 18 K and the capacitor 94 of 56 pf. The required circuitry for the pins 27, 28 and 29 is shown as including the capacitor 96 of 0.15 f, the capacitor 98 of 0.24 f and the resistor 99 of 1.8 M.

As shown in FIG. 9, the input $V_o$ from the output of the circuit of FIG. 2 is introduced to the IN HI pin 34 through resistor 100, which may be of 1M, and across the capacitor 102, which may be 0.002 f.

What is claimed is:

1. A method for measuring the capacitance of a variable capacitor, comprising the steps of:

providing a fixed reference capacitor;

charging said variable capacitor to a fixed voltage during a first, setup phase of a repetitive two phase measuring cycle;

charging said reference capacitor to a variable output voltage during said setup phase;

connecting said capacitors in series in a closed loop during a second, sampling phase of said measuring cycle;

detecting the difference between the potential at a junction between said capacitors after a redistribution of charges in said sampling phase and a predetermined potential established as a balance value; and iteratively varying said output voltage for the next setup phase in a direction to tend to reduce the difference detected in the next sampling phase so that when a difference of zero is detected the magnitude of the output voltage will be indicative of the capacitance of said variable capacitor.

2. A method for measuring the capacitance of a variable capacitor, comprising the steps of:

providing a fixed reference capacitor;

charging said variable capacitor to a fixed voltage during a first, setup phase of a repetitive two phase measuring cycle;

charging said reference capacitor to a variable output voltage during said setup phase;

connecting said capacitors in a series loop with a fixed sampling voltage source in a second, sampling phase of said measuring cycle;

detecting the difference between the potential at the junction between said capacitors after a redistribution of charges in said sampling phase and a predetermined potential established as a balance value; and iteratively varying said output voltage for the next setup phase in a direction to tend to reduce the difference detected in the next sampling phase so that when a difference of zero is detected the magnitude of the output voltage will be indicative of the capacitance of said variable capacitor.

3. A method for measuring the capacitance of a variable capacitor, comprising the steps of:

connecting the variable capacitor in series with a reference capacitor to form a network having a single node at the point of connection of the two capacitors;

connecting across said network during a first phase of a repetitive two phase measuring cycle a feed back output voltage representative of the value of the capacitance being measuring to charge said capacitors in one sense;

clamping said node at a fixed potential during said first phase to establish a fixed voltage across said variable capacitor;

unclamping said node and connecting across said network during a second phase of a two phase measuring cycle a sampling voltage to charge said capacitors in an opposite direction;

integrating during the first of said phases the deviation of said node from said fixed voltage, as a result of switching to the previous one of said second phases, to produce as a result of said integration over a plurality of said measuring cycles said output voltage as a measure of the variable capacitance.

4. The method of claim 3 which includes the steps of connecting a second reference capacitor to said node; and switching the other terminal of said second reference capacitor to put said reference capacitor in series with said variable capacitor across said sampling voltage when the series combination of the first of said reference capacitors and the variable capacitor are connected in series across said output voltage and to be in series with said variable capacitor across said sampling voltage in an opposite sense when the series combination of the first of said reference capacitors and the variable capacitor are connected across said sampling potential.

5. Apparatus for measuring the capacitance of a variable capacitor, comprising:

a reference capacitor having a fixed capacitance;

a sampling voltage source providing a fixed voltage;

a fixed voltage source providing another fixed voltage of smaller magnitude than said sampling voltage;

an output voltage source providing a variable output voltage representative of the measured capacitance;

means operable to connect said variable capacitor across said fixed voltage source to charge said variable capacitor to said other fixed voltage and to connect said reference capacitor across said output voltage source to charge said reference capacitor to the output voltage during a first, setup phase of a repetitive two phase measuring cycle;

means operable to connect said capacitors in a loop with said sampling voltage source in a second, sampling phase of said measuring cycle to allow a redistribution of charges between said capacitors;

means for detecting the difference between the voltage across said reference capacitor as a result of said redistribution of charges in said sampling phase and a predetermined value established as a balance value and for iteratively varying the output voltage produced by said output voltage source for the next setup phase in a direction and to an extent to tend to reduce said difference to zero so that when a difference of zero is reached the magnitude of the output voltage will be indicative of the capacitance of said variable capacitor.

6. A circuit for measuring the capacitance of a variable capacitor comprising:

an output voltage source;

a reference capacitor connected at a node to said variable capacitor to form a series network;

means operable to clamp said node at a fixed voltage during a first of the two phases of a measuring cycle;

a sampling voltage source;

means for connecting said output voltage source across said network during said first of said phases to charge said capacitors and for connecting said sampling voltage source across said network during the second of said phases to charge said capacitors in an opposite direction;

said output voltage source including an integrating amplifier having a high impedance input connected to said node and operable to produce an output voltage in one of said phases, said amplifier being so constructed that its output voltage is the integral of that change in the potential at said node which occurs upon switching from said one of said two phases to the other with the output voltage being in sense to tend to reduce said change in potential for a particular value of capacitance of said variable capacitor so that said output voltage will, after reducing said change to zero represent the capacitance of the variable capacitor.

7. A circuit as set forth in claim 6 in which the means for connecting the sampling and output voltages across the network is an automatic switching means timed by a clock circuit so that the two phases of the measuring cycle are not overlapping.

8. A circuit for measuring the capacitance of a variable capacitor, which comprises:

a reference potential source;

first and second reference capacitors;

a two phase non-overlapping clock for providing signals for timing a setup phase and a sampling phase so that they do not overlap;

means for connecting said reference capacitors and said variable capacitor in a network having a single node at which all of said capacitors have one of their terminals connected;

an integrating amplifier circuit having a high impedance input connected to said node and an output which produces a potential proportional to the integral of the change in potential level on said input due to switching to said sampling phase from said setup phase, said amplifier including means responsive to said clock signals for holding said input at a fixed level during said setup phase, means responsive to said clock signals for sampling the potential level at said node during said sampling phase, and means for integrating the change in potential level at said node upon switching to said sampling phase to change said amplifier output potential accordingly during the next setup phase; and switching means operable to connect the output potential of said amplifier to the other terminal of said first reference capacitors, to connect said sampling voltage to the other terminal of said second reference capacitor, and to connect the variable capacitor to circuit common during said setup phase so as to charge said capacitors and, said switching means being operable during said sampling phase to connect so that said capacitors are charged in an opposite direction so that said node changes potential upon switching to said sampling phase, said output voltage being of sense such that the changes in potential of said node are decreased during successive cycles of said clock.

9. A circuit for measuring the capacitance of a variable capacitor, comprising:

a reference capacitor;

a two phase non-overlapping clock providing timing signals for timing two non-overlapping phases of a measuring cycle;

a measuring cycle having a high impedance input which is held at a fixed potential level during the first phase of a measuring cycle and which is allowed to float during the second phase of the measuring cycle so as to produce an output potential which changes directly as a function of the integral of the deviations of the potential level at said input from said fixed value during said second phase;

means connecting a first terminal of said variable capacitor to a first terminal of said reference capacitor and to the input of said measuring circuit;

means for switching the other terminal of said variable capacitor between a first potential during the first phase of a measurement cycle and a second potential during the second phase of said measuring cycle; and means for switching the other terminal of said reference capacitor between the potential at the output of said measuring circuit during the first phase of the measuring cycle and said first potential during the second phase of the measuring cycle so that as the capacitance of said variable capacitor changes the output of said measuring circuit changes to tend to maintain the potential level at said input during said second phase at the fixed value at which it is maintained during the first phase, whereby the output potential of said measuring circuit is a function of the capacitance of said variable capacitor.

10. A method for measuring the capacitance of a variable capacitor, comprising the steps of:

providing at least one fixed reference capacitor;

connecting said reference capacitor in circuit with said variable capacitor so as to form, at a single common connection, a circuit node;

charging at least one of said capacitors to a fixed voltage during a first phase of a repetitive two phase measuring cycle while clamping said node at a fixed potential;

connecting said circuit in a closed loop so that said capacitors are in series during the second of said phases;

unclamping said node during said second phase to allow redistribution of the charges between said capacitors;

detecting the change of potential at said node due to the unclamping of said node during said second phase;

automatically modifying the charge in said circuit over a number of measuring cycles in response to the detected change of potential at said node, said modification being in direction and extent such that over said number of measuring cycles said detected change is reduced to zero; and integrating the amount the charge is modified over said number of measuring cycles, whereby the integral of said modifications is an indication of the magnitude of the variable capacitance.

11. The method of claim 10 in which the step of modifying the charge is carried out by means of another capacitor connected to said node at one of its terminals and connected to a variable output voltage at its other terminal with the output voltage being modified in response to detected changes in the potential of said node due to its being unclamped so that the output voltage is indicative of said integral.

12. A method for measuring the capacitance of a variable capacitor, comprising the steps of:

providing at least one fixed reference capacitor of known capacitance;

connecting said reference capacitor in circuit with said variable capacitor so as to form, at a single common connection, a circuit node;

charging said capacitors to different voltages during a first phase of a repetitive two phase measuring cycle by placing in series circuit with the circuit combination of said capacitors a fixed voltage source, while clamping said node at a fixed potential;

reversing the polarity of said fixed voltage source in said series circuit during the second of said phases while unclamping said node to allow redistribution of the charges between said capacitors;

detecting the change of the potential at said node after the node is unclamped; and automatically modifying the charge in said circuit in response to the detected change in potential at said node after the node is unclamped, said modification being in direction and extent such that over a number of measuring cycles said detected change is reduced to zero;

integrating the amount the charge is modified over said number of measuring cycles, whereby the integral of said modifications is an indication of the magnitude of the difference between the capacitances of the reference and the variable capacitors and hence the magnitude of the variable capacitance.

13. Apparatus for measuring the capacitance of a variable capacitor, comprising:

at least one fixed capacitor of known capacitance;

means for establishing a predetermined charge on at least oe of said capacitors;

means for connecting said capacitors in a series circuit to allow redistribution of the charges on said capacitors; and means operable in response to the magnitude of said redistribution to modify the charges in said circuit to bring the magnitude of the redistribution to a predetermined value, whereby the amount of modification required is indicative of the capacitance of the variable capacitor.

14. Apparatus as set forth in claim 13 in which the means operable in response to the magnitude of the redistribution of charge is responsive to the deviation from a predetermined value of the potential on a circuit node between said fixed and said variable capacitors.

15. Apparatus as set forth in claim 13 in which said means operable in response to the magnitude of the redistribution of charge operates in one phase of a two phase repetitive measuring cycle to detect said redistribution of charge and in the other phase to change the charge in the circuit to bring the magnitude of the redistribution toward said predetermined value.

16. Apparatus for measuring the capacitance of a variable capacitor, comprising:

first and second reference capacitors, each having a fixed capacitance of known value;

circuit means connecting one side of each of said reference capacitors to one side of said variable capacitor to form at the connection a circuit node;

first and second fixed voltage sources providing first and second fixed voltages;

an output voltage source providing a variable output voltage;

switching means operable during a first phase of a two phase repetitive measuring cycle to connect the other side of said variable capacitor to said first fixed voltage source, to connect the other side of the second reference capacitor to said second fixed voltage source, and to clamp the potential of said node at a fixed value to establish initial charges on said capacitors;

said switching means also being operable during the second phase of said measuring cycle to unclamp said node, to connect the other side of said variable capacitor to said second fixed voltage source, and to connect the other side of the second reference capacitor to said first fixed voltage source to cause a rearrangement of the charges on said capacitors so that for different values of capacitance for said variable capacitor there will result correspondingly different values of change in the potential of said node as it goes from its clamped condition to its unclamped condition;

means connecting said output voltage to the other side of said first reference capacitor so that changes in said output voltage will function to change the magnitude of the change in potential of said node which occurs when it is unclamped; and detecting means connected to said node and operable over successive measuring cycles in response to said change in potential of the node upon the clamping of said node to vary said output voltage in direction and extent tending to reduce said change in potential to zero, whereby said output voltage when said change in potential is zero will be a function of the magnitude of the capacitance of said variable capacitor.

17. Apparatus as set forth in claim 16 in which said first fixed voltage source provides a fixed voltage of zero volts.

18. Apparatus as set forth in claim 16 in which said variable output voltage is connected to the other side of said first reference capacitor only during said first phase of the measuring cycle with said other side of the first reference capacitor being connected to said first fixed voltage source during said second phase of the measuring cycle.

19. A circuit for measuring relative humidity which comprises:
an output voltage source;
a variable capacitor responsive to the humidity of the ambient atmosphere;
a reference capacitor of fixed value;
said variable capacitor and said reference capacitor being manufactured at the same time by a single process so that they will have identical characteristics, said capacitors being integrated onto the same substrate by the simultaneous construction on said substrate of
a first plate for each capacitor,
a dielectric film for each capacitor deposited to overlay said first plate, said dielectric film being of material which changes its dielectric constant with changes in the concentration of water molecules absorbed by the film, and
a second plate for each capacitor deposited to overlay the said dielectric opposite said first plate, said second plate for said variable capacitor being pourous so as to admit water molecules from the ambient atmosphere to the dielectric film, with said second plate for said reference capacitor being impervious to water molecules so that said reference capacitor will not be affected by said water molecules;
means connecting said reference capacitor to said variable capacitor at a node to form a series network;
means operable to clamp said node at a fixed voltage during a first of two phases of a two phase measuring cycle;
a sampling voltage source;
means for connecting said output voltage source across said network during said first of said phases to charge said capacitors and for connecting said sampling voltage source across said network during the second of said phases to charge said capacitors in an opposite directions; and
said output source including an integrating amplifier having a high impedance input connected to said node and operable to produce an output voltage in one of said phases, said amplifier being so constructed that its output voltage is the integral of that change in the potential at said node which occurs upon switching from said one of said two phases to the other with the output voltage being in sense to tend to reduce said change in potential for a particular value of capacitance of said variable capacitor so that said output voltage will, after reducing said change to zero represent the capacitance of the variable capacitor.

20. A circuit as set forth in claim 19 in which said substrate is silicon and all of the circuit elements are constructed as integrated circuit elements on said substrate.

21. A method for measuring the capacitance of a variable capacitor, comprising the steps of:
providing at least one fixed reference capacitor;
connecting said reference capacitor in circuit with the variable capacitor so as to form, at a single common connection, a circuit node;
charging at least one of the capacitors to a fixed voltage during a first phase of a repetitive two phase measuring cycle while clamping said node at a fixed potential;
connecting said circuit in a passive closed loop so that the capacitors are in series during the second of said phases;
unclamping said node during said second phase to allow redistribution of the charges between said capacitors;
detecting the change of potential at said node due to the unclamping of said node during said second phase;
automatically modifying the charge in said circuit in response to the detected change of potential at said node, said modification being in direction and extent such that said detected change is reduced to zero over a number of measuring cycles; and
integrating the amount the charge is modified over said number of measuring cycles, whereby the integral of said modifications is an indication of the magnitude of the variable capacitance.

22. A circuit for measuring humidity, which comprises:
a variable capacitor having a dielectric which changes its dielectric constant with changes in humidity;

a source of sampling potential;
a reference capacitor whose dielectric does not change with changes in humidity;
means for connecting said reference capacitor and said variable capacitor in a network having a single node at which each of said capacitors have one of their terminals connected;
clamping means operable upon selection to clamp said node at a fixed voltage;
feedback means having an input connected to said node and operable to produce an output voltage which is proportional to the integral of the deviation of said node from said fixed voltage when said clamping means is deselected;
switching means whose operation is timed to establish two non-overlapping phases of a repetitive measuring cycle, said switching means being operable during a first of said phases to charge said capacitors to a setup condition by
connecting the output voltage of said feedback means across said network while said sampling potential is disconnected from said network, and
selecting said clamping means so as to hold said node at said fixed potential during said first phase;
said switching means being operable during a second sampling phase to
connect the sampling potential across said network in a polarity opposite to that in which said output voltage was connected during said first phase while said output voltage is disconnected from the network, and
deselect said clamping means so that the node is no longer held at said fixed voltage and so that the resulting change in charge on said capacitors which results from switching from said first to said second phase will cause said node to deviate from said fixed potential in a sense such that the action of said feedback means will cause said output potential to tend toward a value indicative of the value of the capacitance of said variable capacitor;
an indicator for indicating the humidity measured;
an A/D converter circuit having a predetermined number of counts defining the full scale range of said indicator and having differential reference voltage and measured voltage inputs;
a circuit for tailoring the inputs to said converter so that the full scale range and zero offset of the output voltage for the range of humidity being measured generates a full scale indication on said indicator when the output voltage is connected to the high measured input to said converter, said circuit including
an adjustable potentiometer connected across said sampling potential for providing from its adjustable contact the low measured input to said converter,
a voltage divider connected across said sampling voltage to provide at its potential tap a potential representing a factor times said sampling voltage for supplying that potential as an input to the high reference voltage input of said converter, and
another divider circuit connected across a variable portion of said sampling voltage as determined by said adjustable contact and whose tap is connected to one of said reference voltage inputs to said converter with the dividing factor of the divider circuit being proportional to the span of the capacitance range for the variable capacitor over the range to be measured divided by the capacitance at the low end of said range.

23. A circuit as set forth in claim 22 in which the value of said fixed voltage is approximately half the value of said sampling voltage.

24. A circuit as set forth in claim 22 which includes a second reference capacitor; and
said switching means is operable during said first phase to connect the sampling voltage across the series combination of said second reference capacitor and said variable capacitor in sense to produce a flow of charge through said variable capacitor in the same direction as that produced by the connection of said output voltage across the series combination of said first reference capacitor and said variable capacitor, said switching means being operable during said second phase to reverse the connection of said sampling voltage across said series combination of said second reference capacitor and said variable capacitor.

25. A circuit as set forth in claims 23 or 24 in which all of the capacitors in said network are integrated onto a single monolithic substrate by a manufacturing process which produces all of the capacitors of the network at the same time and all of said capacitors have a dielectric which changes its dielectric constant with changes in humidity of the ambient atmosphere and said reference capacitors are protected from the ambient atmosphere so that the capacitance of said reference capacitors is constant.

26. A circuit for measuring the capacitance of a variable capacitor, which comprises:
a source of sampling potential;
a first reference capacitor;
a second reference capacitor;
means for connecting said reference capacitors and said variable capacitor in a network having a single node at which each of said capacitors have one of their terminals connected;
a clock circuit operable to time two non-overlapping phases of repetitive measuring cycles, the first of said phases being a set-up phase and the second phase being the sampling phase;
feedback means made up of
cascaded CMOS logic inverter stages whose input is connected to said node,
clamping means including means operable upon selection for shorting the outputs of said CMOS logic inverters to their respective inputs so as to clamp the input at said node to a fixed potential of value corresponding to the trigger voltage of said logic inverters;
an operational amplifier having a first integrating capacitor connected in its negative feedback path and operable to produce an output voltage, and
a second integrating capacitor connected to be charged up by the output of said logic inverters during said sampling phase and connected to provide the input of said operational amplifier during said setup phase so that said feedback means produces an output voltage which is proportional to the integral of the deviation of said node from said fixed potential when said clamping means is deselected;
switching means operated by said clock circuit during said set-up phase to charge said capacitors to a setup condition by connecting the output voltage of said feedback means to the other terminal of said first reference capacitor, connecting the sampling voltage across the series combination of said second reference capacitor and said variable capacitor in sense to produce a flow of charge through said variable capacitor in the same direction as that produced by the connection of the output voltage across said network, selecting said clamping means so as to hold said node at said fixed potential during said set-up phase;

said switching means being operable during the sampling phase to connect the sampling potential across said network in a polarity opposite to that in which said output voltage was connected during said set-up phase while said output voltage is disconnected from the network, reverse the connection of said sampling voltage across said series combination of said second reference capacitor and said variable capacitor, and deselect said clamping means so that the node is no longer held at said fixed potential and so that the change in charge on said capacitors which results from switching from said first to said second phase will cause said node to deviate from said fixed potential in a sense such that the action of said feedback means will cause said output potential to tend toward a value indicative of the value of the capacitance of said variable capacitor.

* * * * *